(12) United States Patent
Fukuda

(10) Patent No.: US 12,141,977 B2
(45) Date of Patent: Nov. 12, 2024

(54) IMAGE PROCESSING APPARATUS, IMAGE PROCESSING METHOD, AND IMAGE PROCESSING PROGRAM

(71) Applicant: FUJIFILM Corporation, Tokyo (JP)

(72) Inventor: Wataru Fukuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 621 days.

(21) Appl. No.: 17/188,188

(22) Filed: Mar. 1, 2021

(65) Prior Publication Data

US 2021/0183062 A1 Jun. 17, 2021

Related U.S. Application Data

(63) Continuation of application No. PCT/JP2019/029779, filed on Jul. 30, 2019.

(30) Foreign Application Priority Data

Sep. 18, 2018 (JP) ................................ 2018-173715

(51) Int. Cl.
*A61B 6/00* (2024.01)
*A61B 6/50* (2024.01)
*G06T 7/00* (2017.01)

(52) U.S. Cl.
CPC ............ *G06T 7/0014* (2013.01); *A61B 6/481* (2013.01); *A61B 6/482* (2013.01); *A61B 6/502* (2013.01);
(Continued)

(58) Field of Classification Search
CPC ......... A61B 6/502; A61B 6/025; A61B 6/482; A61B 6/5282; A61B 6/5258; A61B 6/481;
(Continued)

(56) References Cited

U.S. PATENT DOCUMENTS

2003/0215057 A1* 11/2003 Trotter ................. G01N 23/046
378/89
2006/0054833 A1* 3/2006 Tsuchino ............. A61B 6/4291
250/370.11
(Continued)

FOREIGN PATENT DOCUMENTS

JP 2005007061 A * 1/2005
JP 2008134205 A * 6/2008
(Continued)

OTHER PUBLICATIONS

An Office Action; "Decision of Refusal," mailed by the Japanese Patent Office on Sep. 20, 2022, which corresponds to Japanese Patent Application No. 2020-548074 and is related to U.S. Appl. No. 17/188,188; with English language translation.
(Continued)

*Primary Examiner* — Chan S Park
*Assistant Examiner* — Woo C Rhim
(74) *Attorney, Agent, or Firm* — Studebaker & Brackett PC

(57) ABSTRACT

An image processing apparatus including: an acquisition unit that acquires a first radiographic image captured by irradiating a subject, in which a contrast agent is administered, with radiation of a first energy and a second radiographic image captured by irradiating the subject with radiation of a second energy; a generation unit that generates a difference image between the first and the second radiographic image; and a correction unit that performs a correction on either one of the first and second radiographic images or the difference image to remove an artifact component which generates an artifact predetermined as an appearance similar to that of a contrast agent imaging by the contrast agent, wherein, in a case in which the correction unit performs the correction on the first and the second radiographic image, the generation unit generates a difference
(Continued)

image between the corrected first and second radiographic image.

5 Claims, 10 Drawing Sheets

(52) U.S. Cl.
CPC .. *A61B 6/5282* (2013.01); *G06T 2207/10124* (2013.01); *G06T 2207/10144* (2013.01); *G06T 2207/20224* (2013.01); *G06T 2207/30068* (2013.01)

(58) Field of Classification Search
CPC .......... A61B 6/484; G06T 2207/30068; G06T 7/0012; G06T 7/0014; G06T 11/005; G06T 2207/10116; G06T 5/50; G06T 2207/10081; G06T 2207/10112; G06T 2210/41; G06T 2207/30004; G06T 2207/10072; G06T 6/481; G06T 6/482; G06T 6/502; G06T 6/5282; G06T 2207/10124; G06T 2207/10144; G06T 2207/20224
See application file for complete search history.

(56) References Cited

U.S. PATENT DOCUMENTS

| | | | | |
|---|---|---|---|---|
| 2007/0242797 | A1* | 10/2007 | Stewart | A61B 6/482 378/16 |
| 2007/0268996 | A1* | 11/2007 | Hagiwara | G01N 23/046 378/4 |
| 2008/0167552 | A1* | 7/2008 | Bouchevreau | A61B 6/482 600/431 |
| 2009/0304253 | A1* | 12/2009 | Puong | G06T 5/50 382/131 |
| 2009/0310886 | A1* | 12/2009 | Kitamura | G06T 5/008 382/275 |
| 2010/0061654 | A1* | 3/2010 | Manak | G06T 5/50 382/275 |
| 2011/0164797 | A1* | 7/2011 | Jang | A61B 6/486 382/130 |
| 2011/0243305 | A1* | 10/2011 | Tada | A61B 6/583 378/207 |
| 2012/0008849 | A1* | 1/2012 | Reboni | G06T 5/002 382/132 |
| 2014/0056497 | A1* | 2/2014 | Hsieh | A61B 6/488 382/131 |
| 2014/0094696 | A1* | 4/2014 | Fukuda | A61B 6/5211 600/425 |
| 2014/0110594 | A1* | 4/2014 | Star-Lack | A61B 6/4233 250/394 |
| 2014/0119495 | A1* | 5/2014 | Jang | A61B 6/4007 378/4 |
| 2014/0119506 | A1* | 5/2014 | Kang | A61B 6/583 378/54 |
| 2014/0321603 | A1* | 10/2014 | Taguchi | A61B 6/405 378/5 |
| 2015/0071403 | A1* | 3/2015 | Ishii | A61B 6/4233 378/36 |
| 2015/0093013 | A1* | 4/2015 | Morita | G16H 50/20 382/132 |
| 2015/0302615 | A1* | 10/2015 | Fukuda | A61B 6/032 378/19 |
| 2016/0151035 | A1* | 6/2016 | Noda | A61B 6/5258 378/26 |
| 2016/0206264 | A1* | 7/2016 | Fukuda | A61B 6/4452 |
| 2016/0206268 | A1* | 7/2016 | Fukuda | A61B 6/5205 |
| 2016/0206269 | A1* | 7/2016 | Jung | A61B 6/5258 |
| 2016/0206271 | A1* | 7/2016 | Han | A61B 6/5235 |
| 2016/0235385 | A1* | 8/2016 | Enomoto | A61B 6/5282 |
| 2016/0249875 | A1* | 9/2016 | Enomoto | A61B 6/467 378/62 |
| 2016/0354051 | A1* | 12/2016 | Enomoto | A61B 6/4241 |
| 2017/0055932 | A1* | 3/2017 | Lee | A61B 6/5264 |
| 2017/0055933 | A1* | 3/2017 | Kawamura | G16H 50/20 |
| 2017/0065241 | A1* | 3/2017 | Hoernig | A61B 6/5235 |
| 2017/0065244 | A1* | 3/2017 | Taki | A61B 6/544 |
| 2017/0086770 | A1* | 3/2017 | Morita | A61B 6/025 |
| 2017/0086773 | A1* | 3/2017 | Kamiya | A61B 6/502 |
| 2017/0231593 | A1* | 8/2017 | Fukuda | A61B 6/482 382/132 |
| 2017/0236276 | A1* | 8/2017 | Fukuda | A61B 6/5252 382/131 |
| 2017/0281108 | A1* | 10/2017 | Choi | A61B 6/5217 |
| 2018/0064408 | A1* | 3/2018 | Shimada | A61B 6/5252 |
| 2018/0240224 | A1 | 8/2018 | Fukuda | |
| 2021/0055233 | A1* | 2/2021 | Noda | A61B 6/482 |

FOREIGN PATENT DOCUMENTS

| | | | |
|---|---|---|---|
| JP | 2008245991 A | * | 10/2008 |
| JP | 2009247553 A | * | 10/2009 |
| JP | 2009-291271 A | | 12/2009 |
| JP | 2009-297393 A | | 12/2009 |
| JP | 2011245117 A | * | 12/2011 |
| JP | 2014-061286 A | | 4/2014 |
| JP | 2015-192846 A | | 11/2015 |
| JP | 2017-143943 A | | 8/2017 |
| JP | 2017189392 A | * | 10/2017 |
| JP | 2018-134205 A | | 8/2018 |
| WO | 2006/030594 A1 | | 3/2006 |

OTHER PUBLICATIONS

An Office Action; "Decision of Dismissal of Amendment," mailed by the Japanese Patent Office on Sep. 20, 2022, which corresponds to Japanese Patent Application No. 2020-548074 and is related to U.S. Appl. No. 17/188,188; with English language translation.
International Search Report issued in PCT/JP2019/029779; mailed Oct. 29, 2019.
International Preliminary Report on Patentability and Written Opinion issued in PCT/JP2019/029779; issued Mar. 23, 2021.
An Office Action; "Notice of Reasons for Refusal", mailed by the Japanese Patent Office on Mar. 22, 2022, which corresponds to Japanese Patent Application No. 2020-548074 and is related to U.S. Appl. No. 17/188,188; with English language translation.
An Office Action; "Notice of Reasons for Refusal", mailed by the Japanese Patent Office on Sep. 21, 2021, which corresponds to Japanese Patent Application No. 2020-548074 and is related to U.S. Appl. No. 17/188,188; with English language translation.
The extended European search report issued by the European Patent Office on Sep. 21, 2021, which corresponds to European Patent Application No. 19861828.2-1126 and is related to U.S. Appl. No. 17/188,188.

* cited by examiner

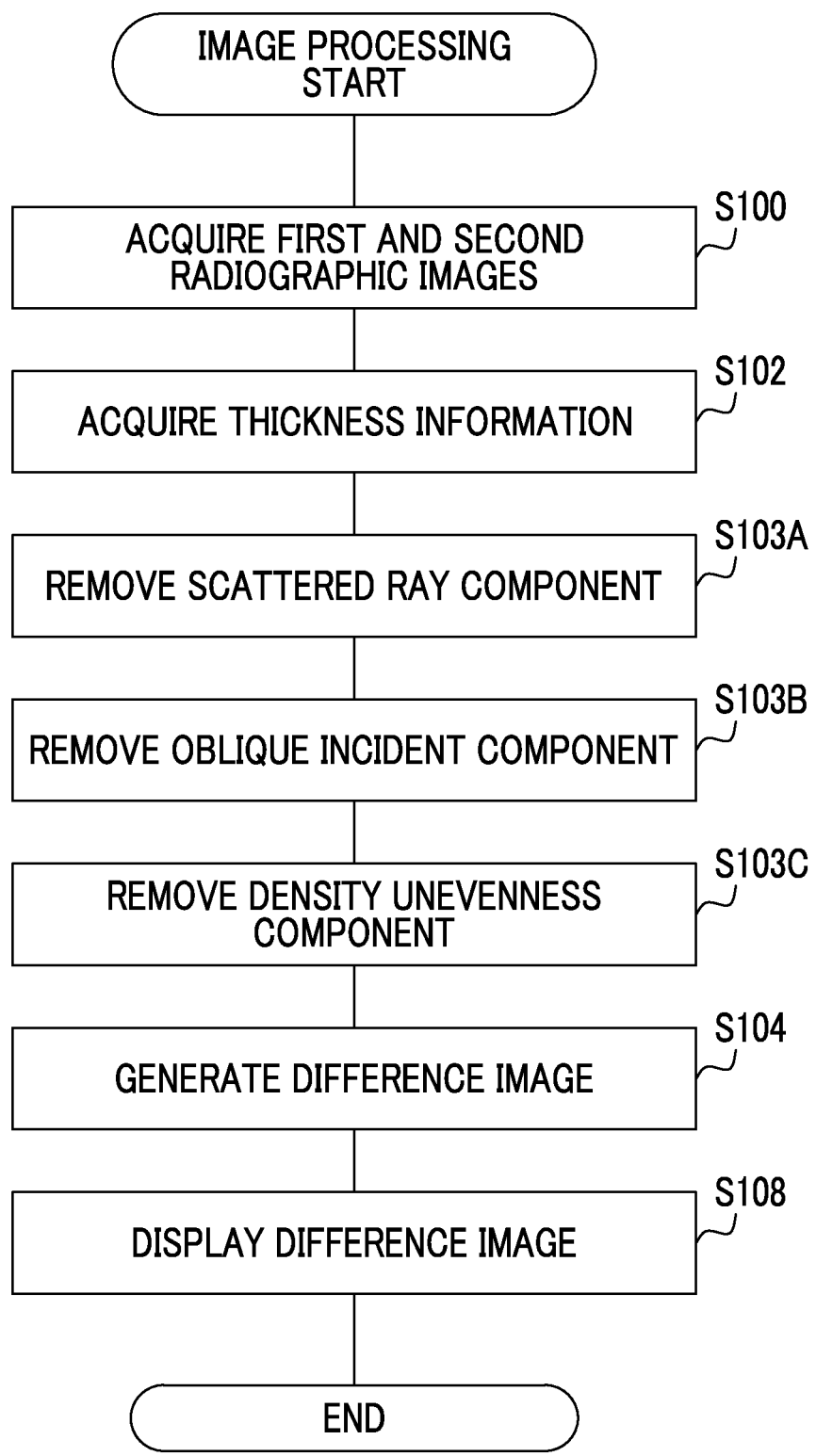

IMAGE PROCESSING APPARATUS, IMAGE PROCESSING METHOD, AND IMAGE PROCESSING PROGRAM

CROSS-REFERENCE TO RELATED APPLICATIONS

This application is a continuation application of International Application No. PCT/JP2019/029779, filed on Jul. 30, 2019, which is incorporated herein by reference in its entirety. Further, this application claims priority from Japanese Patent Application No. 2018-173715, filed on Sep. 18, 2018, the disclosure of which is incorporated by reference herein.

BACKGROUND

Technical Field

The present disclosure relates to an image processing apparatus, an image processing method, and an image processing program.

Related Art

There is known a radiography apparatus that irradiates a subject such as a breast of an examinee from a radiation source with radiation and detects the radiation transmitted through the subject with a radiation detector to capture a radiographic image. As the radiography apparatus, there is also known a technique for generating a difference image between the first radiographic image obtained by irradiating a subject in a state in which a contrast agent is administered with radiation of the first energy and the second radiographic image obtained by irradiating a subject with radiation of the second energy different from the first energy.

For example, Japanese Patent Application Laid-Open (JP-A) No. 2017-143943 discloses a technique for acquiring the first radiographic image, which is captured under the first imaging condition, and the second radiographic image, which is obtained by reconstructing a projection image captured under the second imaging condition, of a breast in a state in which a contrast agent is administered by a mammography apparatus, and generating a difference image between the first radiographic image and the second radiographic image.

In a difference image, a human body structure such as a mammary gland is de-emphasized and a contrast agent is emphasized in the image, but an artifact having an appearance similar to an image of a contrast agent component (hereinafter referred to as "contrast agent imaging") may occur. This type of artifact may occur in the vicinity of a skin line of a subject, for example, and may be difficult to distinguish from the contrast agent imaging.

In the technique disclosed in JP-A 2017-143943, an image quality is improved by removing a scattered ray component from a projection image, but it is not sufficient to suppress the occurrence of the artifact described above, and it is sometimes difficult to distinguish the contrast agent imaging from the artifact.

SUMMARY

The present disclosure provides an image processing apparatus, an image processing method, and an image processing program capable of improving the appearance of the contrast agent imaging.

The first aspect of the present disclosure is an image processing apparatus comprising an acquisition unit that acquires the first radiographic image captured by irradiating a subject in a state in which a contrast agent is administered with radiation of the first energy and the second radiographic image captured by irradiating the subject with radiation of the second energy different from the first energy, a generation unit that generates a difference image between the first radiographic image and the second radiographic image, and a correction unit that performs a correction on either one of the first and second radiographic images or the difference image to remove an artifact component which generates an artifact predetermined as an appearance similar to that of a contrast agent imaging by the contrast agent, in which in a case in which the correction unit performs the correction on the first radiographic image and the second radiographic image, the generation unit generates a difference image between the corrected first radiographic image and the corrected second radiographic image.

According to the second aspect of the present disclosure, in the first aspect, the correction unit may perform a correction to remove, as the artifact component, an oblique incident component caused by an oblique incidence of the radiation onto the subject.

According to the third aspect of the present disclosure, in the first aspect or the second aspect, the correction unit may perform the correction to remove, as the artifact component, a scattered ray component caused by a scattered ray of radiation.

According to the fourth aspect of the present disclosure, in any one aspect of the first aspect to third aspect, the correction unit may perform the correction to remove, as the artifact component, density unevenness caused by a radiation irradiation apparatus that irradiates the subject with the radiation.

According to the fifth aspect of the present disclosure, in any one of the first aspect to third aspect, the correction unit may perform the correction with a correction amount corresponding to a thickness of the subject with respect to an incidence direction of the radiation.

According to the sixth aspect of the present disclosure, in any one aspect of the first aspect to third aspect, the correction unit may perform the correction to remove a lower frequency component as a thickness of the subject with respect to an incidence direction of the radiation is thicker.

According to the seventh aspect of the present disclosure, in any one aspect of the first aspect to fourth aspect, in a case of performing the correction on the difference image, as the correction to remove the artifact component, the correction unit may generate a contrast agent component removed image in which a contrast agent component is removed from the difference image, and generate a contrast agent image which is a difference between the difference image and the contrast agent component removed image.

According to the eighth aspect of the present disclosure, in the seventh aspect, the correction unit may remove the contrast agent component by combining a plurality of different types of processing.

In the ninth aspect of the present disclosure, in any one aspect of the first aspect to the eighth aspect, the subject may be a human breast.

The tenth aspect of the present disclosure is an image processing method executed by a computer, the method comprising acquiring the first radiographic image captured by irradiating a subject in a state in which a contrast agent is administered with radiation of the first energy and the second radiographic image captured by irradiating the subject with radiation of the second energy different from the first energy, generating a difference image between the first radiographic image and the second radiographic image, and performing a correction on either the first and second radiographic image or the difference image to remove an artifact component which generates an artifact predetermined as an appearance similar to that of a contrast agent imaging by the contrast agent, in which in a case of performing the correction on the first radiographic image and the second radiographic image, a difference image between the corrected first radiographic image and the corrected second radiographic image is generated.

The eleventh aspect of the present disclosure is an image processing program for causing a computer to execute a process, the process comprising acquiring the first radiographic image captured by irradiating a subject in a state in which a contrast agent is administered with radiation of the first energy and the second radiographic image captured by irradiating the subject with radiation of the second energy different from the first energy, generating a difference image between the first radiographic image and the second radiographic image, and performing a correction on either the first and second radiographic images or the difference image to remove an artifact component which generates an artifact predetermined as an appearance similar to that of a contrast agent imaging by the contrast agent, in which in a case in which the correction unit performs the correction on the first radiographic image and the second radiographic image, the generation unit generates a difference image between the corrected first radiographic image and the corrected second radiographic image.

The twelfth aspect of the present disclosure is an image processing apparatus having a processor, the processor including processes of acquiring the first radiographic image captured by irradiating a subject in a state in which a contrast agent is administered with radiation of the first energy and the second radiographic image captured by irradiating the subject with radiation of the second energy different from the first energy, generating a difference image between the first radiographic image and the second radiographic image, and performing a correction on either the first and second radiographic images or the difference image to remove an artifact component which generates an artifact predetermined as an appearance similar to that of a contrast agent imaging by the contrast agent, in which in a case in which the correction unit performs the correction on the first radiographic image and the second radiographic image, the generation unit generates a difference image between the corrected first radiographic image and the corrected second radiographic image.

According to the above aspect, the image processing apparatus, the image processing method, and the image processing program of the present disclosure can improve the appearance of the contrast agent imaging.

BRIEF DESCRIPTION OF DRAWINGS

FIG. 10B is a flowchart showing another example of a flow of image processing executed on a console of the third exemplary embodiment.

DESCRIPTION OF EMBODIMENTS

Hereinafter, exemplary embodiments of the present invention will be described in detail with reference to the drawings. It should be noted that the present exemplary embodiment does not limit the present invention.

First Embodiment

Figure 1:
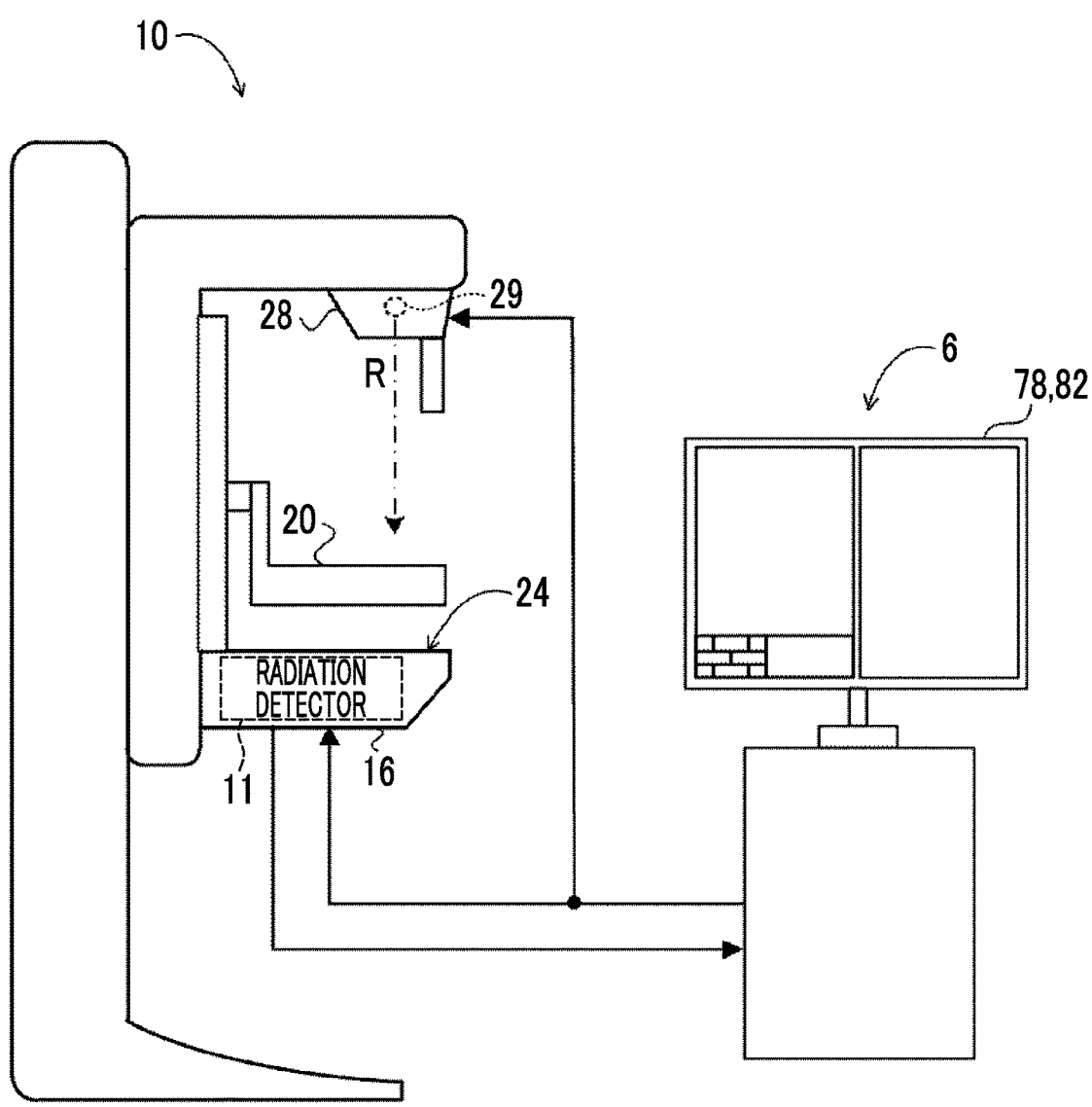
FIG. 1 is a configuration diagram schematically showing an example of an overall configuration of a radiographic imaging system of the first exemplary embodiment.

First, an example of an overall configuration of the radiographic imaging system of the present exemplary embodiment will be described. FIG. 1 shows a configuration diagram showing an example of the overall configuration of a radiographic imaging system 1 of the present exemplary embodiment.

The radiographic imaging system 1 of the present exemplary embodiment has a function of capturing a radiographic image by an operation of a user such as a doctor or a radiologist on the basis of an instruction (imaging order) input from an external system (for example, radiology information system (RIS)) via a console 6.

Figure 2:
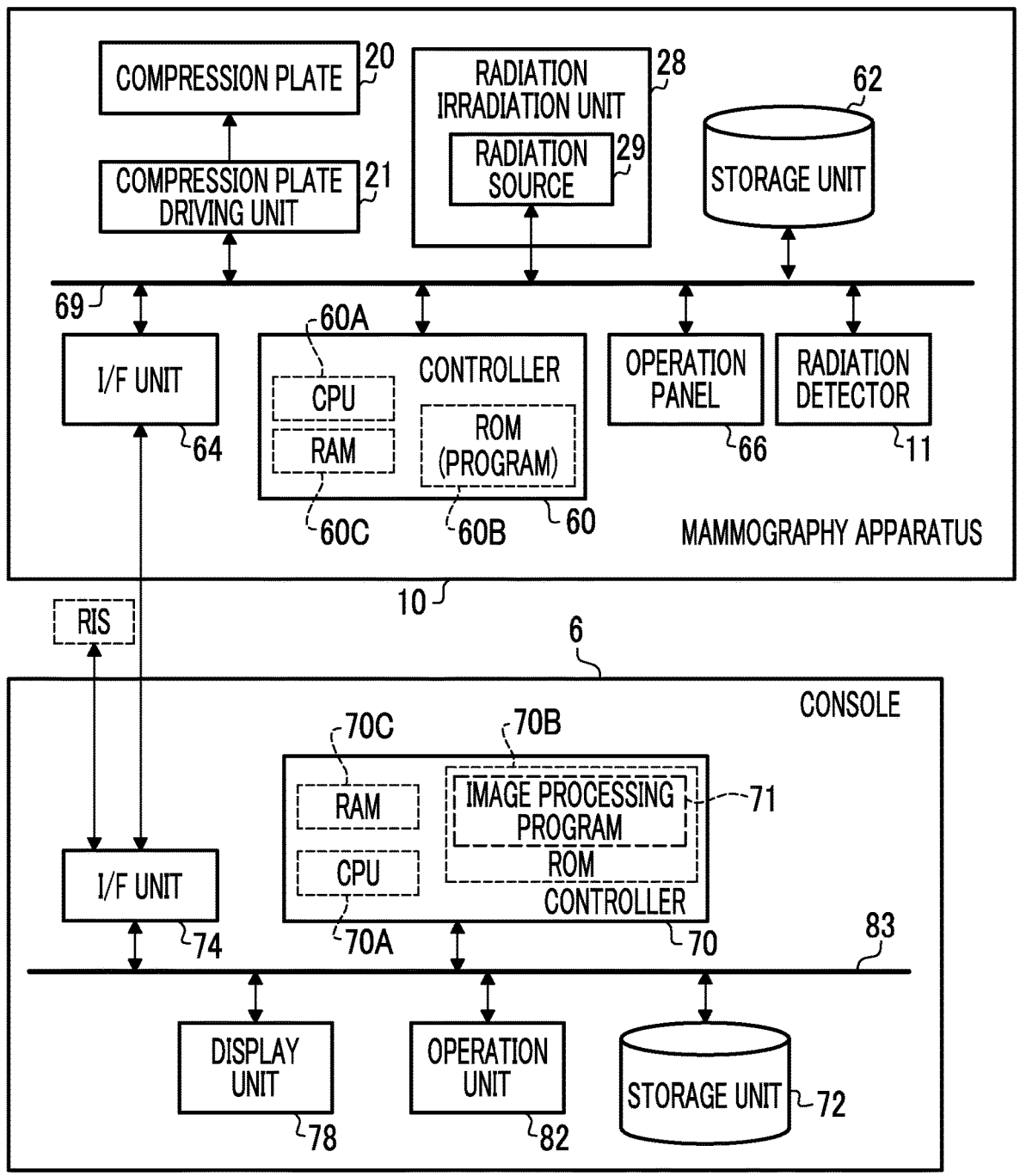
FIG. 2 is a block diagram showing an example of a configuration of a console and a mammography apparatus according to the first exemplary embodiment.

As shown in FIG. 1, the radiographic imaging system 1 of the present exemplary embodiment comprises the console 6 and a mammography apparatus 10. FIG. 2 shows a block diagram showing an example of the configuration of the console 6 and the mammography apparatus 10 of the present exemplary embodiment.

The mammography apparatus 10 of the present exemplary embodiment is an apparatus for capturing a radiographic image of a breast of an examinee, as a subject, by irradiating the breast with radiation R (for example, X-rays). In addition, the mammography apparatus 10 may be an apparatus that images the breast of the examinee not only in a state in which the examinee is standing (standing position state) but also in a state in which the examinee sits on a chair (including a wheelchair) or the like (sitting position state).

Further, the mammography apparatus 10 of the present exemplary embodiment has a function of performing contrast imaging by energy subtraction imaging as a function of performing so-called contrast imaging in which imaging is performed in a state in which the contrast agent is administered to the breast of the examinee, and has, for example, a contrast enhanced digital mammography (CEDM) function.

It should be noted that in the mammography apparatus 10 of the present exemplary embodiment, in energy subtraction imaging, radiation R of the first energy is irradiated from a radiation source 29 of a radiation irradiation unit 28, and the first radiographic image is obtained by a radiation detector 11. In addition, the radiation source 29 is irradiated with radiation R having the second energy different from that of the first energy, and the second radiographic image is obtained by the radiation detector 11. As an example, in the present exemplary embodiment, the first energy is higher than the second energy. In the present exemplary embodiment, in a case in which the first radiographic image, the second radiographic image, and a difference image described in detail later are collectively referred to without distinction, they are simply referred to as "radiographic image". It should be noted that irradiating the radiation R of the first energy means irradiating the radiation R from the radiation source 29 by applying a tube voltage corresponding to the first energy, and similarly, irradiating the radiation R of the second energy means irradiating the radiation R from the radiation source 29 by applying a tube voltage corresponding to the second energy.

As shown in FIG. 2, the mammography apparatus 10 of the present exemplary embodiment comprises the radiation detector 11, a compression plate driving unit 21 for driving a compression plate 20, the radiation irradiation unit 28 having the radiation source 29, a controller 60, a storage unit 62, an interface (I/F) unit 64, and an operation panel 66. The radiation detector 11, the compression plate driving unit 21, the radiation irradiation unit 28, the controller 60, the storage unit 62, the I/F unit 64, and the operation panel 66 are connected to each other such that various information can be transmitted and received via a bus 69 such as a system bus or a control bus.

The controller 60 of the present exemplary embodiment controls the overall operation of the mammography apparatus 10 in response to the control (instruction) of the console 6. The controller 60 comprises a central processing unit (CPU) 60A, a read only memory (ROM) 60B, and a random access memory (RAM) 60C. The ROM 60B stores in advance various programs and the like, which are executed by the CPU 60A and include an imaging processing program for controlling the imaging of radiographic images. The RAM 60C temporarily stores various types of data.

The storage unit 62 stores image data of the radiographic image captured by the radiation detector 11 and various other information. Specific examples of the storage unit 62 include a hard disk drive (HDD) and a solid state drive (SSD). The I/F unit 64 communicates various information with the console 6 by wireless communication or wired communication. The operation panel 66 is provided, for example, as a plurality of switches on an imaging table (not shown) of the mammography apparatus 10. It should be noted that the operation panel 66 may be provided as a touch panel.

The radiation detector 11 detects the radiation R that has passed through the breast, which is the subject. The radiation detector 11 generates the radiographic image on the basis of the detected radiation R, and outputs image data representing the generated radiographic image. The type of the radiation detector 11 of the present exemplary embodiment is not particularly limited, and may be, for example, an indirect conversion type radiation detector that converts radiation R into light and converts the converted light into electric charge, or a direct conversion type radiation detector that converts radiation R into electric charge directly. In the present exemplary embodiment, the image data representing a radiographic image output from the radiation detector 11 of the mammography apparatus 10 is transmitted to the console 6.

On the other hand, the console 6 of the present exemplary embodiment has a function of controlling the mammography apparatus 10 by using an imaging order, various types of information acquired from an external system or the like via a wireless communication local area network (LAN) or the like, and instructions or the like made by a user through an operation unit 82 (refer to FIG. 2), an irradiation instruction button (not shown) or the like to be described later.

The console 6 of the present exemplary embodiment is, for example, a server computer. As shown in FIG. 2, the console 6 comprises a controller 70, a storage unit 72, an I/F unit 74, a display unit 78, and an operation unit 82. The controller 70, the storage unit 72, the I/F unit 74, the display unit 78, and the operation unit 82 are connected to each other through a bus 83, such as a system bus or a control bus, so as to be able to transmit and receive various types of information. The console 6 of the present exemplary embodiment is an example of the image processing apparatus of the present disclosure.

The controller 70 of the present exemplary embodiment controls the overall operation of the console 6. The controller 70 comprises a CPU 70A, a ROM 70B, and a RAM 70C. Various programs including an image processing program 71, which will be described later, executed by the CPU 70A are stored in the ROM 70B in advance. The RAM 70C temporarily stores various types of data.

The storage unit 72 stores image data of the radiographic image captured by the mammography apparatus 10 and various other information. Specific examples of the storage unit 72 include an HDD, an SSD, and the like.

The display unit 78 displays various information. The operation unit 82 is used for the user to input instructions and various information related to capturing a radiographic image including an exposure instruction of radiation R. The operation unit 82 is not particularly limited, and for example, various switches, a touch panel, a touch pen, a mouse, and the like are exemplified. It should be noted that the operation unit 82 and the display unit 78 may be integrated into a touch panel display.

The I/F unit 74 communicates various information with the external system such as the mammography apparatus 10 or RIS by wireless communication or wired communication. In addition, the I/F unit 74 receives the image data of the radiographic image from the mammography apparatus 10 by wireless communication or wired communication.

Figure 3:
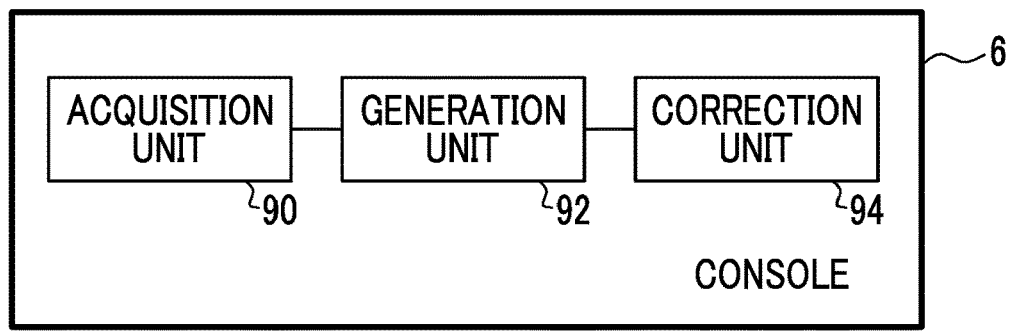
FIG. 3 is a functional block diagram of an example of a console configuration according to the first exemplary embodiment.

FIG. 3 is a functional block diagram of an example of a configuration of the console 6 according to the present exemplary embodiment. As shown in FIG. 3, the console 6 of the present exemplary embodiment comprises an acquisition unit 90, a generation unit 92, and a correction unit 94.

The acquisition unit 90 acquires the first radiographic image and the second radiographic image. As an example, the acquisition unit 90 of the present exemplary embodiment acquires image data representing each of the first radiographic image and the second radiographic image from the storage unit 72. It should be noted that an acquisition destination in which the acquisition unit 90 acquires the first radiographic image and the second radiographic image is not limited to the present exemplary embodiment, and may acquire the first radiographic image and the second radiographic image from, for example, the mammography apparatus 10, or from an external apparatus such as a picture archiving and communication system ((PACS) not shown).

The generation unit 92 generates a difference image in which the contrast agent imaging is emphasized from each image data of the first radiographic image and the second radiographic image. As an example, the generation unit 92 of the present exemplary embodiment generates image data of a difference image by multiplying a value obtained by subtracting image data (pixel value) of the second radiation for each corresponding pixel from image data (each pixel value) of the first radiographic image by a weight coefficient. In the present exemplary embodiment, as an example, a weight coefficient on the basis of a mammary gland absorption coefficient $\mu g^H$ for radiation R of the first energy, a fat absorption coefficient $\mu a^H$ for radiation R of the first energy, a mammary gland absorption coefficient $\mu g^L$ for radiation R of the second energy, and a fat absorption coefficient $\mu a^L$ for radiation R of the second energy is used. Specifically, a weight coefficient α obtained by the equation (1) is used.

$$\alpha = (\mu g^L \mu a^L)/(\mu g^H \mu a^H) \tag{1}$$

It should be noted that a method by which the generation unit 92 generates the difference image is not limited to the method of the present exemplary embodiment, and a known method for generating the difference image can be used.

The correction unit 94 performs a correction on either the first and second radiographic images or the difference image to remove an artifact component that generates an artifact predetermined as an appearance similar to that of the contrast agent imaging by the contrast agent. As an example, the correction unit 94 of the present exemplary embodiment performs a correction to remove, from the difference image, as artifact components, the oblique incident component caused by the oblique incidence of the radiation R onto the subject and a scattered ray component caused by the scattered ray of the radiation R.

Figure 4:
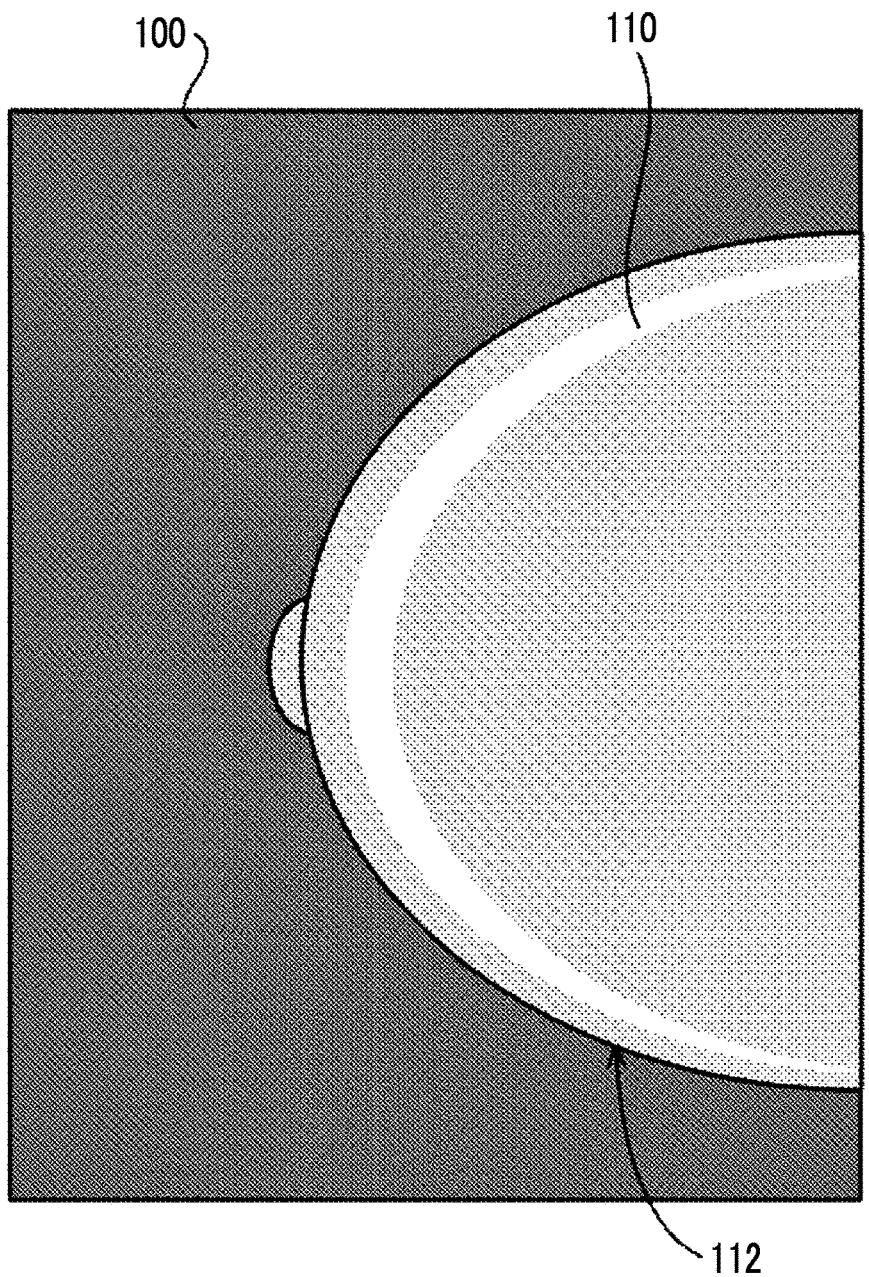
FIG. 4 is a diagram showing an example of a difference image in a state in which an artifact occurs.

FIG. 4 shows an example of the difference image 100 in the state in which the artifact is generated. As in the example shown in FIG. 4, in the difference image 100, an artifact 110 appears white. In particular, a white band-shaped artifact 110 may occur in the vicinity of a skin line 112. The white band-shaped artifact 110 tends to appear strongly near the nipple. Since a contrast agent imaging portion also appears white in the difference image 100, in a case in which the artifact 110 is generated, it may be difficult to determine whether the white region in the difference image 100 is due to the contrast agent imaging or the artifact 110.

There are two main causes for the occurrence of the above artifact 110.

Figure 5:
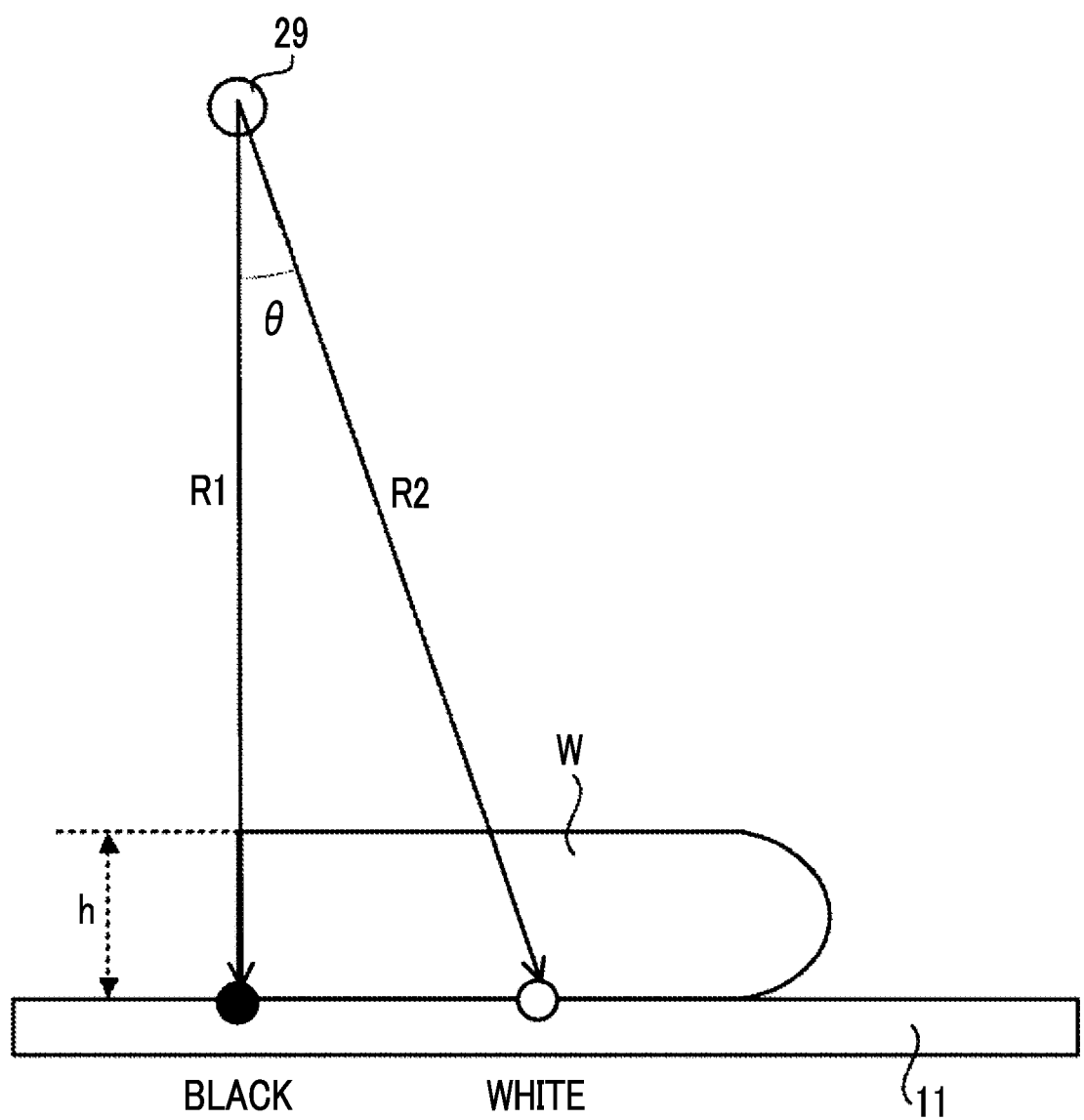
FIG. 5 is a schematic diagram for illustrating an example of an artifact by an oblique incident component of radiation.

The first cause is the oblique incident component caused by the oblique incidence of radiation R onto the subject. FIG. 5 shows a schematic diagram for illustrating an example of an artifact due to the oblique incident component of radiation R. In a case in which the radiation R1 having an incidence angle of 0 degrees from the radiation source 29 is incident on a breast W having a thickness h, a length of a transmission path through which the radiation R1 passes through the breast W becomes h. On the other hand, in a case in which the radiation R2 having an incidence angle of θ is incident from the radiation source 29, the length of the transmission path is h/cos θ. Therefore, the transmission path in a case in which the radiation R2 is incident is longer than the transmission path in a case in which the radiation is incident by R1 by the length x minutes represented by the equation (2).

$$x = (1/\cos\theta - 1) \times h \tag{2}$$

The longer the transmission path, the smaller a dose of radiation R reaching the radiation detector 11. Therefore, the radiation R2 has a smaller dose of the radiation R that passes through the breast W and reaches the radiation detector 11 than the radiation R1. Since the dose is reduced, an image generated by the radiation detector 11 according to the radiation R2 is whiter than an image generated by the radiation detector 11 according to the radiation R1. As shown in the equation (2), a pixel value of the radiographic image becomes smaller according to the oblique incidence of the radiation R. In addition, as the thickness h of the breast W becomes thicker, the transmission path becomes longer and the pixel value of the radiographic image becomes smaller. Therefore, the oblique incident component of the radiation R becomes the artifact component.

Figure 6:
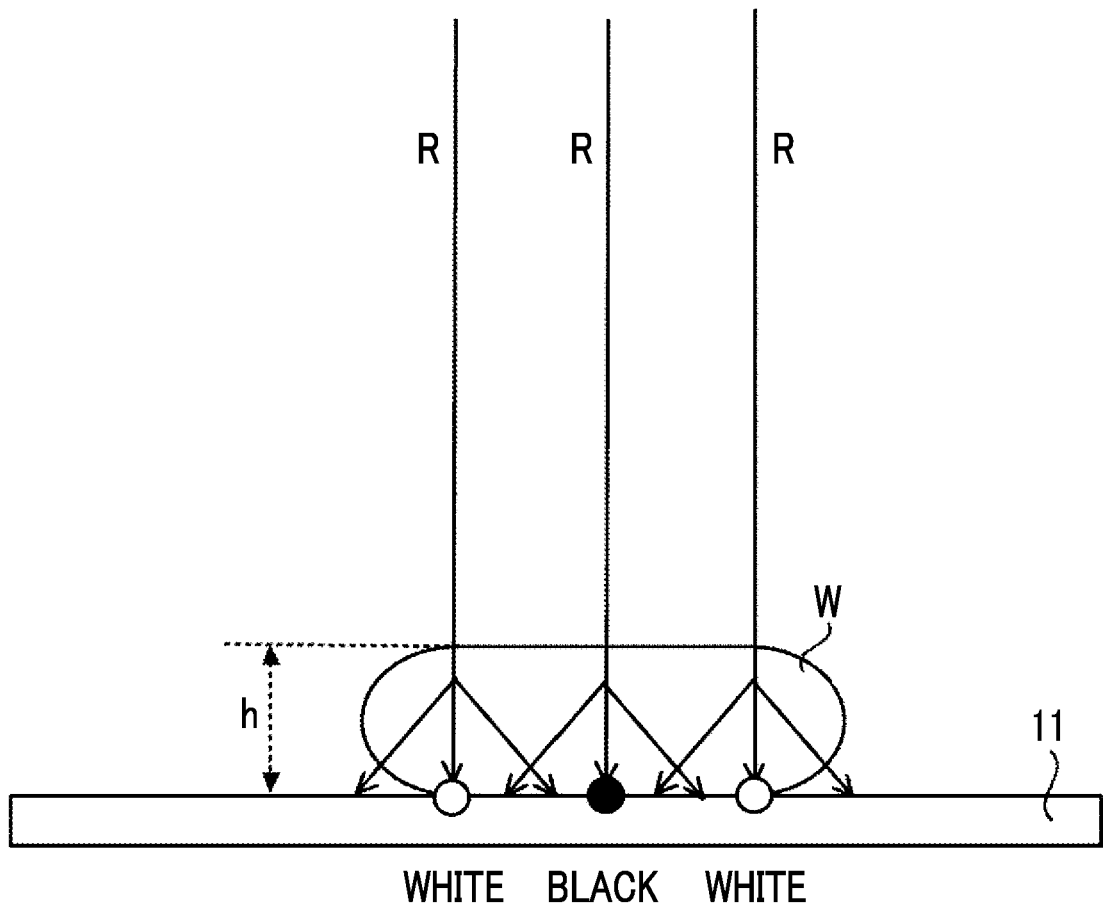
FIG. 6 is a schematic diagram for illustrating an example of an artifact by a scattered ray component of radiation.

The second cause is the scattered ray component caused by the scattered ray of radiation R. FIG. 6 shows a schematic diagram for illustrating an example of the artifact by the scattered ray component of radiation R. An image of a region inside the breast W is increased in the dose since the scattered ray generated by the breast W overlaps. Therefore, a pixel value of the image in the region inside the breast W becomes large, and the image becomes black. On the other hand, in an image of a region at an end portion of the breast W, a part of the scattered ray escapes to the outside of the breast W, so that the dose is reduced. Therefore, a pixel value of an image on the end portion side of the breast, in other words, a region on the skin line side, becomes small and the image becomes white. In other words, in the vicinity of the skin line of the breast W, the pixel value becomes smaller than that in an internal region. In the case of the breast W, since the scattered ray is difficult to escape to the outside on a chest wall side, the dose increases and the pixel value increases, so that the image tends to be black. On the other hand, on the nipple side, the scattered ray easily escapes to the outside, so that the dose is small and the pixel value is small, so that the image tends to be white. Therefore, the scattered ray component of the radiation R becomes an artifact component. It should be noted that the thicker the thickness h of the breast W is, the more scattered ray is generated.

Therefore, as described above, the correction unit 94 of the present exemplary embodiment removes the artifact component by performing a correction to remove the oblique incident component and the scattered ray component from the difference image generated by the generation unit 92.

Next, the operation of the console 6 of the present exemplary embodiment will be described with reference to the drawings.

First, contrast imaging with the mammography apparatus 10 of the present exemplary embodiment will be described. In a case of performing the contrast imaging in the mammography apparatus 10 of the present exemplary embodiment, the user first positions the breast W in a state in which the contrast agent is administered to the examinee on an imaging surface of an imaging table 16 of the mammography apparatus 10. In a case in which the positioning is completed, the compression plate 20 is driven by the compression plate driving unit 21, and the breast W is compressed and immobilized between the compression plate 20 and the imaging surface 24 of the imaging table 16. The mammography apparatus 10 of the present exemplary embodiment has a function of detecting the thickness h of the breast W in a state of being compressed by the compression plate 20. As an example, the mammography apparatus 10 of the present exemplary embodiment detects a distance between the compression plate 20 and the imaging surface 24 of the imaging table 16 as the thickness h of the breast W according to the amount of drive by which the compression plate driving unit 21 drives the compression plate 20.

In a case in which irradiation of radiation R is instructed by pressing an irradiation instruction button (not shown) provided on the console 6 by a user, the mammography apparatus 10 irradiates the radiation R of the first energy toward a breast from the radiation source 29 in response to control of the console 6, and generates the first radiographic image by the radiation detector 11. In addition, in a case in which the irradiation of the radiation R is instructed by the user, the mammography apparatus 10 irradiates the breast with the radiation R of the second energy from the radiation source 29, and generates the second radiographic image by the radiation detector 11. The generated first radiographic image and second radiographic image are transmitted from the mammography apparatus 10 to the console 6 in a state associated with information representing the thickness h of the breast W. The console 6 stores the received first radiographic image and second radiographic image in the storage unit 62 in a state in which the information representing the thickness h of the breast W is associated with each other.

In a case in which the first radiographic image and the second radiographic image are generated, the compression plate driving unit 21 drives the compression plate 20 in a direction away from the breast W, that is, in a direction approaching the radiation source 29 to release the compression of the breast W.

Figure 7:
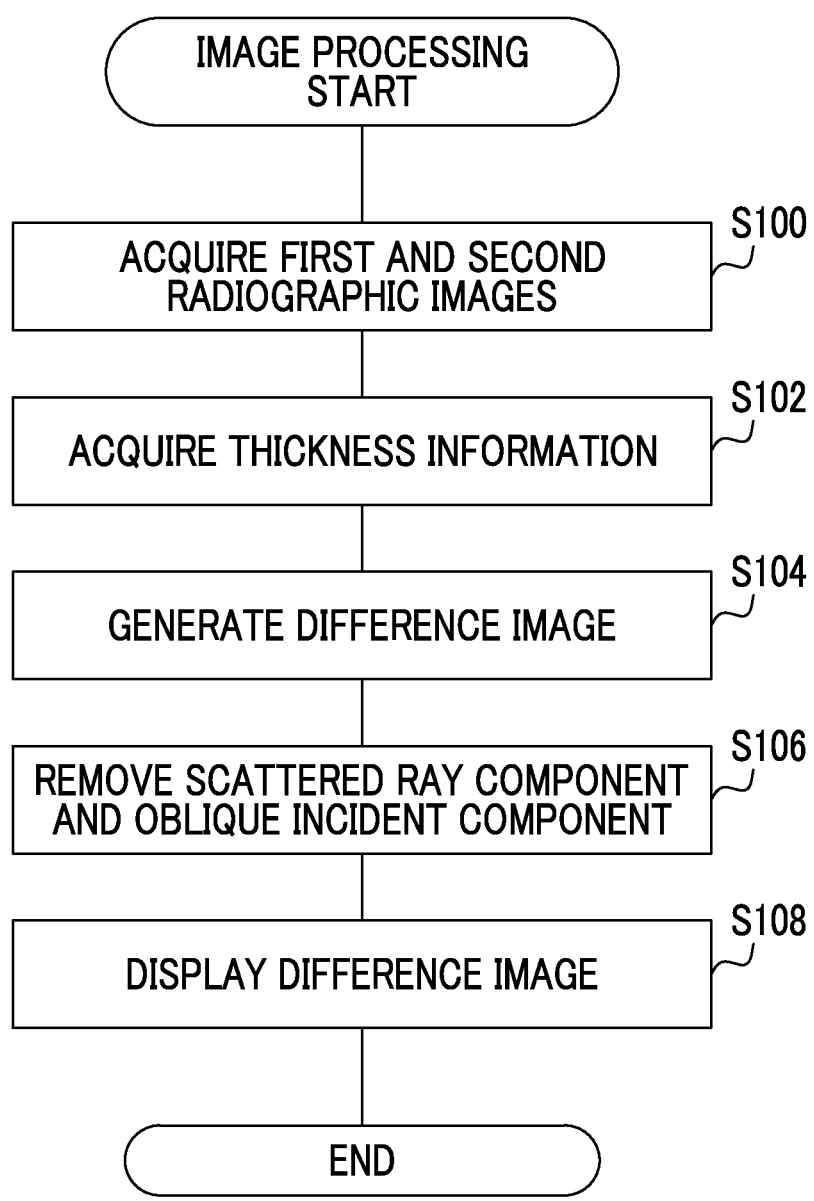
FIG. 7 is a flowchart showing an example of a flow of image processing executed on a console of the first exemplary embodiment.

In this way, the console 6 performs the image processing shown in FIG. 7 on the first radiographic image and the second radiographic image obtained by the contrast imaging by the mammography apparatus 10. Specifically, in a case in which the console 6 receives the instruction to display the radiographic image obtained by imaging by the user via the operation unit 82 or the like, the console 6 executes the image processing shown in FIG. 7 as an example. FIG. 7 shows a flowchart showing an example of the flow of image processing executed by the console 6 of the present exemplary embodiment. In the console 6 of the present exemplary embodiment, the CPU 70A of the controller 70 executes the image processing program 71 stored in the ROM 70B to execute the image processing shown in FIG. 7, and the CPU 70A functions as each of the acquisition unit 90, the generation unit 92, and the correction unit 94.

In Step S100, the acquisition unit 90 acquires the first radiographic image and the second radiographic image to be displayed. In the present exemplary embodiment, as described above, the acquisition unit 90 acquires the image data of the first radiographic image and the image data of the second radiographic image from the storage unit 72.

In the next Step S102, the acquisition unit 90 acquires information representing the thickness h of the breast W in the contrast imaging. In the present exemplary embodiment, information representing the thickness h of the breast W associated with the first radiographic image and the second radiographic image acquired in Step S100 is acquired from the storage unit 72.

In the next Step S104, the generation unit 92 generates a difference image between the first radiographic image and the second radiographic image. As described above, the generation unit 92 of the present exemplary embodiment generates the difference image using the weight coefficient a represented by the equation (1).

In the next Step S106, the correction unit 94 removes the scattered ray component and the oblique incident component from the difference image generated in the Step S104. The scattered ray component and the oblique incident component occur as low frequency unevenness. Therefore, the correction unit 94 of the present exemplary embodiment removes the scattered ray component and the oblique incident component from the difference image by applying a low frequency removal filter for removing the low frequency component corresponding to the scattered ray component and the oblique incident component to the difference image. As described above, since the degree of the scattered ray component and the oblique incident component changes according to the thickness h of the breast W, specifically, since the scattered ray component and the oblique incident component increase as the breast W is thicker, it is preferable to apply the low frequency removal filter that removes a lower frequency component as the breast W is thicker. In the present exemplary embodiment, a plurality of low frequency removal filters are prepared according to the thickness h of the breast W. On the basis of the information representing the thickness h of the breast W acquired in Step S102, the correction unit 94 applies the corresponding low frequency removal filter to remove the scattered ray component and the oblique incident component from the difference image. It should be noted that a threshold value of the low frequency removal filter may be changed in response to the scattered ray component, the oblique incident component, the user's instruction, and the like.

In the next Step S108, the correction unit 94 causes the display unit 78 to display the difference image from which the scattered ray component and the oblique incident component have been removed. In a case in which the difference image is displayed on the display unit 78 by the present step, the present image processing is ended.

Therefore, in the console 6 of the present exemplary embodiment, in order to remove the scattered ray component and the oblique incident component from the difference image, the difference image in which the scattered ray component and the oblique incident component are removed, and the contrast agent imaging is emphasized is displayed on the display unit 78.

Second Exemplary Embodiment

Hereinafter, the second exemplary embodiment will be described in detail.

The overall configuration of the radiographic imaging system 1 and the configuration of each of the console 6 and the mammography apparatus 10 are the same as those of the first exemplary embodiment, and therefore the description thereof is omitted. In the present exemplary embodiment, since a part of the image processing executed by the console 6 is different from the image processing executed by the console 6 of the first exemplary embodiment (refer to FIG. 7) with respect to the first radiographic image and the second radiographic image obtained by the contrast imaging with the mammography apparatus 10, different processing will be described.

Figure 8:
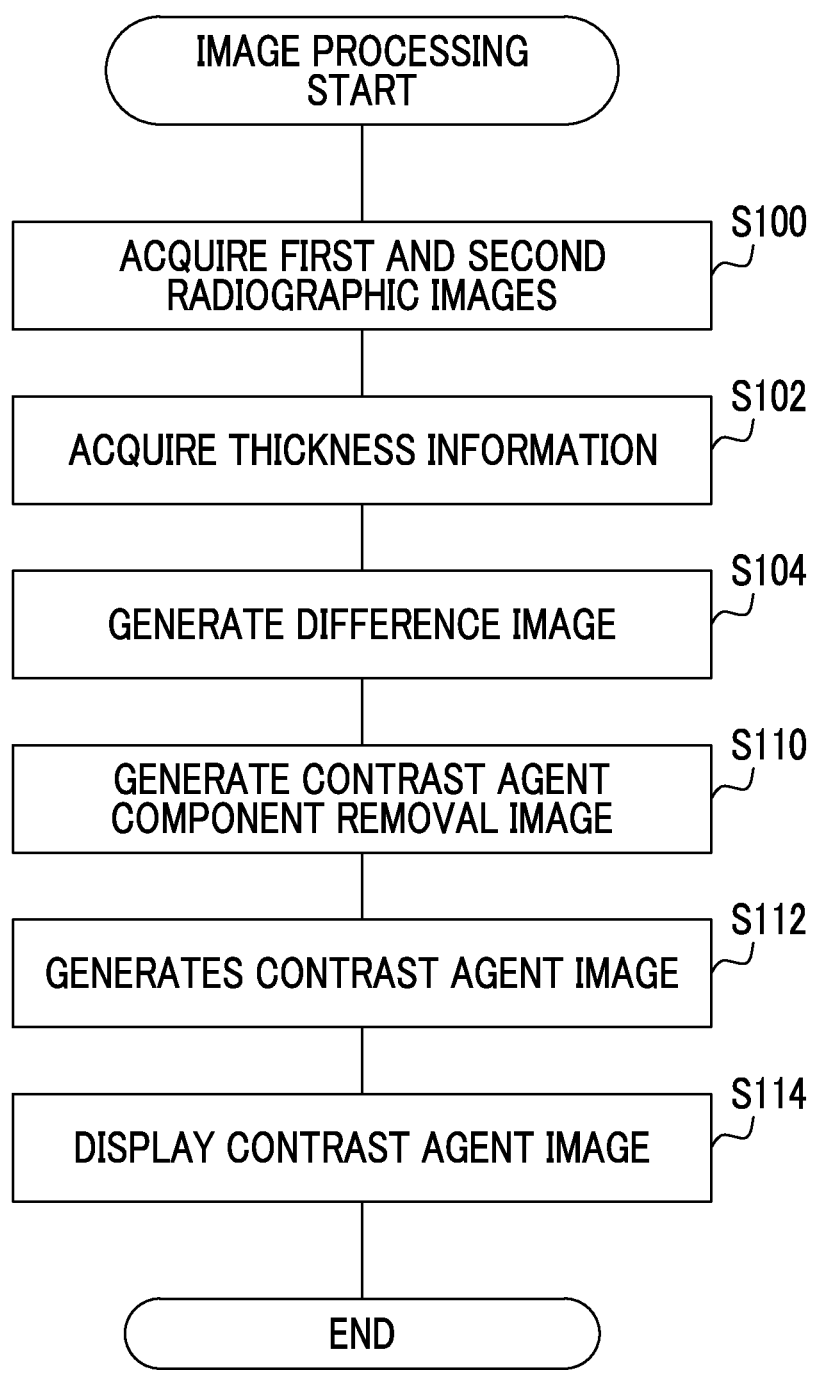
FIG. 8 is a flowchart showing an example of a flow of image processing executed on a console of the second exemplary embodiment.

FIG. 8 shows a flowchart showing an example of the flow of image processing executed by the console 6 of the present exemplary embodiment. The image processing shown in FIG. 8 is different in that the processing of Step S110 to Step S114 is executed instead of Step S106 and Step S108 of the image processing (refer to FIG. 7) of the first exemplary embodiment.

In Step S110 shown in FIG. 8, the correction unit 94 generates an image in which the contrast agent component is removed (hereinafter, referred to as "contrast agent component removed image") from the difference image generated in Step S104. As an example, the correction unit 94 of the present exemplary embodiment uses a combination of a plurality of types of processing for removing the contrast agent component from the difference image.

The contrast agent component has a higher frequency component than the oblique incident component and the scattered ray component described above. Therefore, the correction unit 94 of the present exemplary embodiment removes the contrast agent component from the difference image by applying a high frequency removal filter for removing high frequency component corresponding to the contrast agent component to the difference image as one of the plurality of types of processing. The thicker the breast W, the smaller the pixel value of the contrast agent imaging and the whiter the image since the contrast agent administered to the breast W appears to overlap. As described above, since the contrast agent imaging is affected by the thickness h of the breast W, as an example, the correction unit 94 of the present exemplary embodiment applies the high frequency removal filter corresponding to the thickness h of the breast W to remove the contrast agent component. As the high frequency removal filter in this case, for example, a high frequency component removal filter having the same threshold value as a low frequency component removal filter described in the first exemplary embodiment may be applied.

Further, since the contrast agent stains structures such as lesions and blood vessels deeply, the correction unit 94 of the present exemplary embodiment applies a structure detection model (not shown) in which the structure stained deeply by the contrast agent is learned to detect the structure stained deeply in the difference image and removes a region of the detected structure from the difference image to remove the contrast agent component as one of the plurality of types of processing described above.

The structure detection model is a learned model in which the difference image obtained by contrast imaging is input and information representing the structure to be deeply stained by the contrast agent in the input difference image is output. The information representing the structure to be deeply stained by the contrast agent includes, for example, information such as a lesion such as a mass and the structure, shape, and position of a blood vessel. The structure detection model is constructed by machine learning using, as learning data, a plurality of data pairs in which image analysis results of the difference image obtained by the contrast imaging are used as teaching data and the information representing the structure to be deeply stained by the contrast agent is made into a pair as the output data. It should be noted that it is also preferable to further use information representing the thickness h of the breast W as the teaching data. A machine learning method is not particularly limited, and for example, known machine learning methods such as a support vector machine (SVM), a gaussian mixture model (GMM), a hidden markov model (HMM), and a neural network (NN) are applied.

In addition, since the scattered ray component and the oblique incident component are related to the shape of the breast W as described above, the correction unit 94 of the present exemplary embodiment removes the contrast agent component from the difference image by removing a structure that does not correspond to the scattered ray component and the oblique incident component included in the difference image detected by applying a component detection model (not shown) in which the scattered ray component and the oblique incident component derived from the shape of the breast W are learned, from the difference image as one of the plurality of types of processing.

The component detection model is a learned model in which the difference image obtained by the contrast imaging is input and the information representing the scattered ray component and the oblique incident component in the input difference image is output. The component detection model is constructed by machine learning using, as the learning data, a plurality of data pairs in which image analysis results of the difference image obtained by the contrast imaging are used as teaching data and the information representing the scattered ray component and the oblique incident component is made into a pair as output data. It should be noted that it is also preferable to further use information representing the thickness h of the breast W as the teaching data. The machine learning method is not particularly limited, and for example, known machine learning methods such as SVM and HMM are applied.

The correction unit 94 of the present exemplary embodiment removes the contrast agent component from the difference image by combining the above three types of processing and applying it to the difference image. As an example, the correction unit 94 of the present exemplary embodiment combines the processing results obtained by performing each of the three types of processing on the difference image obtained in Step S104.

The combination of the three types of processing is not limited to the present exemplary embodiment and may be, for example, an aspect in which the three types of processing are sequentially performed in a random order, in other words, an aspect in which the next processing is performed on the image obtained as a processing result of the previous processing. In addition, the order of processing in this case is not particularly limited. For example, in a case in which the structure detection model described above is applied to an image obtained by removing a high frequency component from the difference image to detect a structure to be deeply stained by the contrast agent, the teaching data of the applied structure detection model is preferably an image obtained by removing the high frequency component from the difference image. In addition, any one of the above three types of processing may be performed. Further, a method of generating the contrast agent component removed image from the difference image is not limited to the present exemplary embodiment.

In the next Step S112, the correction unit 94 generates a contrast agent image. The correction unit 94 generates a contrast agent image including a contrast agent imaging by generating an image of difference between the difference image generated in Step S104 and the contrast agent component removed image generated in Step S110. Specifically, the correction unit 94 generates a contrast agent image by subtracting the image data (pixel value) of the contrast agent component removed image from the image data (each pixel value) of the difference image for each corresponding pixel. It should be noted that the "contrast agent imaging" is an image of the contrast agent component as described above, and refers to an image of only a portion of the contrast agent component extracted from the radiographic image. On the other hand, the "contrast agent image" refers to the entire radiographic image including the contrast agent imaging from which the scattered ray component and the oblique incident component are removed.

The contrast agent image generated by the correction unit 94 of the present exemplary embodiment is an image in which the contrast agent imaging is emphasized more than the difference image in which the scattered ray component and the oblique incident component generated in the first exemplary embodiment are removed.

In the next Step S114, the correction unit 94 causes the display unit 78 to display the contrast agent image generated in the Step S112. In a case in which the contrast agent image is displayed on the display unit 78 by this step, the present image processing is ended.

In order to remove the scattered ray component and the oblique incident component from the difference image in this way, in Step S114, the correction unit 94 removes the scattered ray component and the oblique incident component, and displays the contrast agent image which is a contrast agent imaging on the display unit 78.

In the console 6 of the present exemplary embodiment, as described above, from the difference image, a contrast agent image is generated by removing (subtracting) the contrast agent component removed image obtained by combining a plurality of types of processing for removing the contrast agent component from the difference image. That is, the contrast agent image of the present exemplary embodiment is a combination of the contrast agent imaging obtained for each of a plurality of types of processing in the generation of the contrast agent component removed image. Therefore, according to the console 6 of the present exemplary embodiment, a contrast agent image including a contrast agent imaging having higher accuracy than the contrast agent imaging obtained by one type of processing can be obtained.

Third Exemplary Embodiment

Hereinafter, the third exemplary embodiment will be described in detail.

The overall configuration of the radiographic imaging system 1 and the configuration of each of the console 6 and the mammography apparatus 10 are the same as those of the first exemplary embodiment, and therefore the description thereof is omitted. In the present exemplary embodiment, since a part of the image processing executed by the console 6 is different from the image processing executed by the console 6 of the first exemplary embodiment (refer to FIG. 7) with respect to the first radiographic image and the second radiographic image obtained by the contrast imaging with the mammography apparatus 10, different processing will be described.

Figure 9:
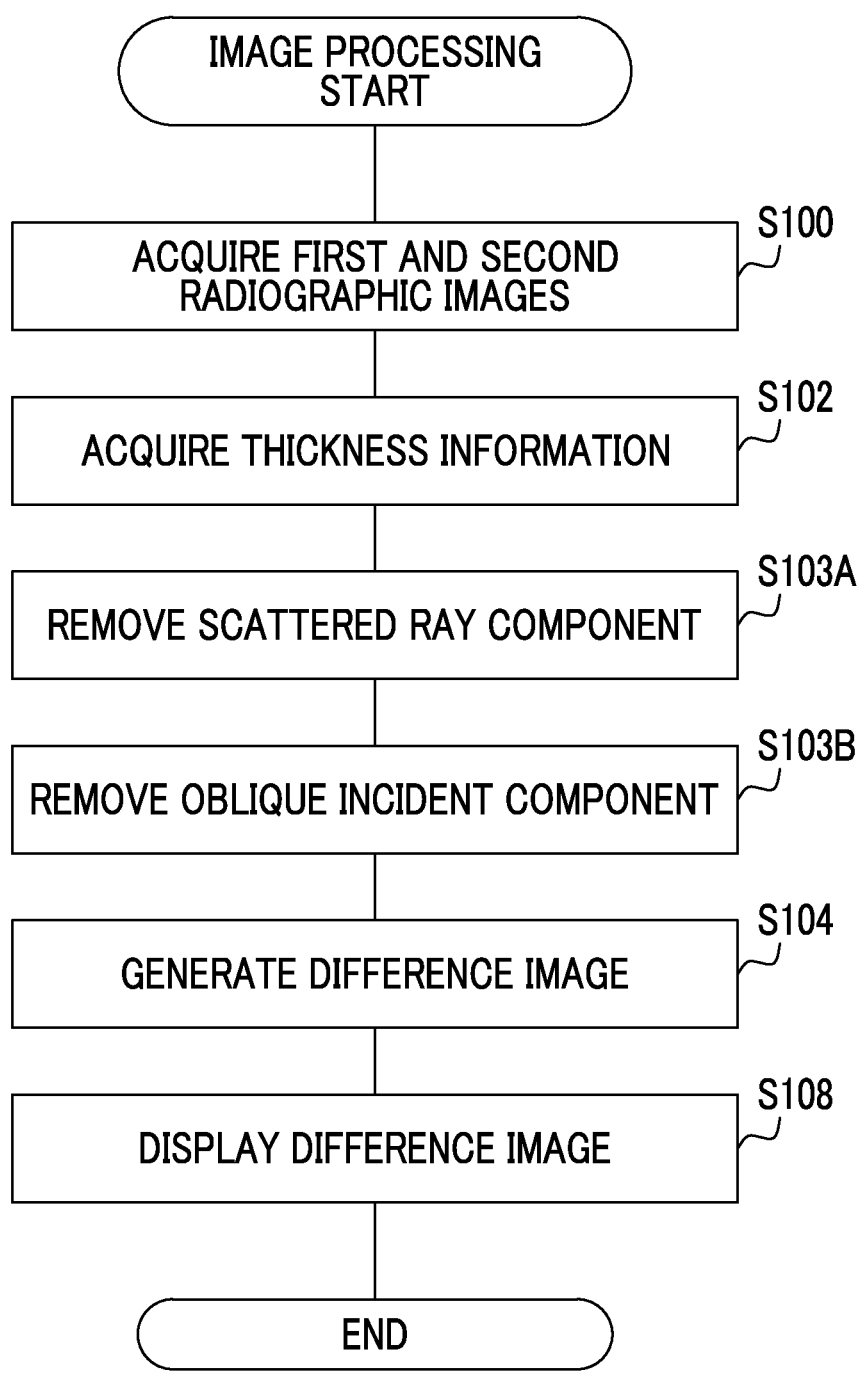
FIG. 9 is a flowchart showing an example of a flow of image processing executed on a console of the third exemplary embodiment.

FIG. 9 shows a flowchart showing an example of the flow of image processing executed by the console 6 of the present exemplary embodiment. The image processing shown in FIG. 9 is different in that the processing of Step S103A and Step S103B are executed between Step S102 and Step S104 instead of Step S106 of the image processing (refer to FIG. 7) of the first exemplary embodiment.

In Step S103A shown in FIG. 9, the correction unit 94 removes the scattered ray component from each of the first radiographic image and the second radiographic image acquired in Step S100. As an example, in the console 6 of the present exemplary embodiment, a plurality of pieces of scattered ray component correction data obtained in advance according to various conditions such as thickness h are stored in the storage unit 72 in advance using a phantom simulating the breast W. Then, the correction unit 94 acquires the scattered ray component correction data corresponding to the thickness h of the breast W from the storage unit 72, and removes the scattered ray component by correcting the difference image using the acquired scattered ray component correction data. It should be noted that the method by which the correction unit 94 removes the scattered ray component is not limited to the method of the present exemplary embodiment, and a known method for removing the scattered ray component can be used.

In Step S103B, the correction unit 94 removes the oblique incident component from each of the first radiographic image and the second radiographic image from which the scattered ray component has been removed by the processing of Step S103A. As described above, the oblique incident component is determined according to an incidence angle θ of the radiation R irradiated from the radiation source 29 and the thickness h of the breast W. The transmission path becomes longer according to the thickness h of the breast W and the position of the radiation source 29 (incidence angle θ of the radiation R) in the contrast imaging. Therefore, as an example, the correction unit 94 of the present exemplary embodiment removes the oblique incident component on the basis of an attenuation amount of the radiation R corresponding to the thickness h of the breast and the incidence angle θ of the radiation R from each of the first radiographic image and the second radiographic image. Therefore, in the mammography apparatus 10 of the present exemplary embodiment associates the image data of each of the first radiographic image and the second radiographic image with information such as a source image distance (SID) and incidence angle θ in the contrast imaging and transmits them to the console 6.

The method by which the correction unit 94 removes the oblique incident component is not limited to the method of the present exemplary embodiment, and for example, correction information such as a correction map corresponding to the difference image for correcting the oblique incident component may be stored in the storage unit 72 in association with the thickness h of the breast W, and the correction unit 94 may correct the oblique incident component on the basis of the correction information stored in the storage unit 72.

As described above, in the present exemplary embodiment, the correction unit 94 removes the scattered ray component and the oblique incident component from each of the first radiographic image and the second radiographic image. Therefore, in Step S104 of the present exemplary embodiment, the generation unit 92 generates a difference image from the first radiographic image from which the scattered ray component and the oblique incident component are removed and the second image from which the scattered ray component and the oblique incident component are removed. As an example, the method of generating the difference image by the generation unit 92 of the present exemplary embodiment is the same as that of Step S104 of the image processing (see FIG. 7) of the first exemplary embodiment.

Therefore, the difference image displayed by the correction unit 94 on the display unit 78 in the next Step S108 is the difference image in which the scattered ray component and the oblique incident component are removed and the contrast agent imaging is emphasized.

The order of the processing in Step S103A and the processing in Step S103B is not particularly limited, and the processing in Step S103B may be performed first, in other words, the removal of the scattered ray component may be performed after the removal of the oblique incident component.

As described above, the console 6 of each of the exemplary embodiments comprises the acquisition unit 90 that acquires the first radiographic image captured by irradiating the breast W in a state in which a contrast agent is administered with radiation R of the first energy and the second radiographic image captured by irradiating the subject with radiation R of the second energy different from the first energy, the generation unit 92 that generates the difference image between the first radiographic image and the second radiographic image, and the correction unit 94 that performs the correction on either the first and second radiographic images or the difference image to remove the artifact component which generates the artifact predetermined as an appearance similar to that of the contrast agent imaging by the contrast agent. In a case in which the correction unit 94 corrects the first radiographic image and the second radiographic image, the generation unit 92 generates a difference image between the corrected first radiographic image and the corrected second radiographic image.

According to the console 6 of each of the above exemplary embodiment, the scattered ray component and the oblique incident component are removed as an example of the artifact component. Therefore, according to the console 6 of each of the above exemplary embodiments, the appearance of the contrast agent imaging can be improved.

Further, according to the console 6 of the first exemplary embodiment and the second exemplary embodiment, the scattered ray component and the oblique incident component are removed from the difference image. Since the difference image is an image from which the mammary gland structure or the like is removed, it is easier to detect and remove the scattered ray component and the oblique incident component than a case in which removing the scattered ray component and the oblique incident component from the first radiographic image and the second radiographic image.

It should be noted that the correction unit 94 may remove the artifact component that generates the artifact predetermined as an appearance similar to that of the contrast agent imaging by the contrast agent with respect to either the first and second radiographic images or the difference image, and the specific artifact component to be removed is not limited to each of the above exemplary embodiments.

For example, the cause of the above artifact 110 is not limited to the above-described two causes. As an example of other causes, there is a density unevenness component caused by the radiation irradiation unit 28 that irradiates the radiation R. Examples of this type of density unevenness include a density unevenness corresponding to a heel effect caused by a radiation tube (not shown) comprised in the radiation source 29 of the radiation irradiation unit 28. The heel effect is a phenomenon in which the radiation R is absorbed by a material itself of an anode of the radiation tube, so that a radiation irradiated to a cathode side becomes higher dose and lower energy than the radiation irradiated to the anode side. Due to the effect of the heel effect, in a region where the dose of radiation R is small, the pixel value becomes small, so that the image tends to be white and appears as a density unevenness in the radiographic image. The heel effect tends to be more pronounced with lower energy radiation.

Therefore, since the density unevenness component caused by the heel effect is the artifact component, the correction unit 94 of the console 6 may remove an influence of the density unevenness component caused by the heel effect from the radiographic image. It should be noted that the method by which the correction unit 94 removes the influence of the density unevenness component caused by the heel effect is not particularly limited, and for example, a known technique such as that disclosed in JP2009-297393A can be used. JP2009-297393A discloses a technique of estimating an irradiation unevenness component on the basis of a distribution of pixel values in a direction (direction connecting the anode and cathode of the radiation tube) in which the heel effect appears, and correcting the estimated irradiation unevenness.

Figure 10A:
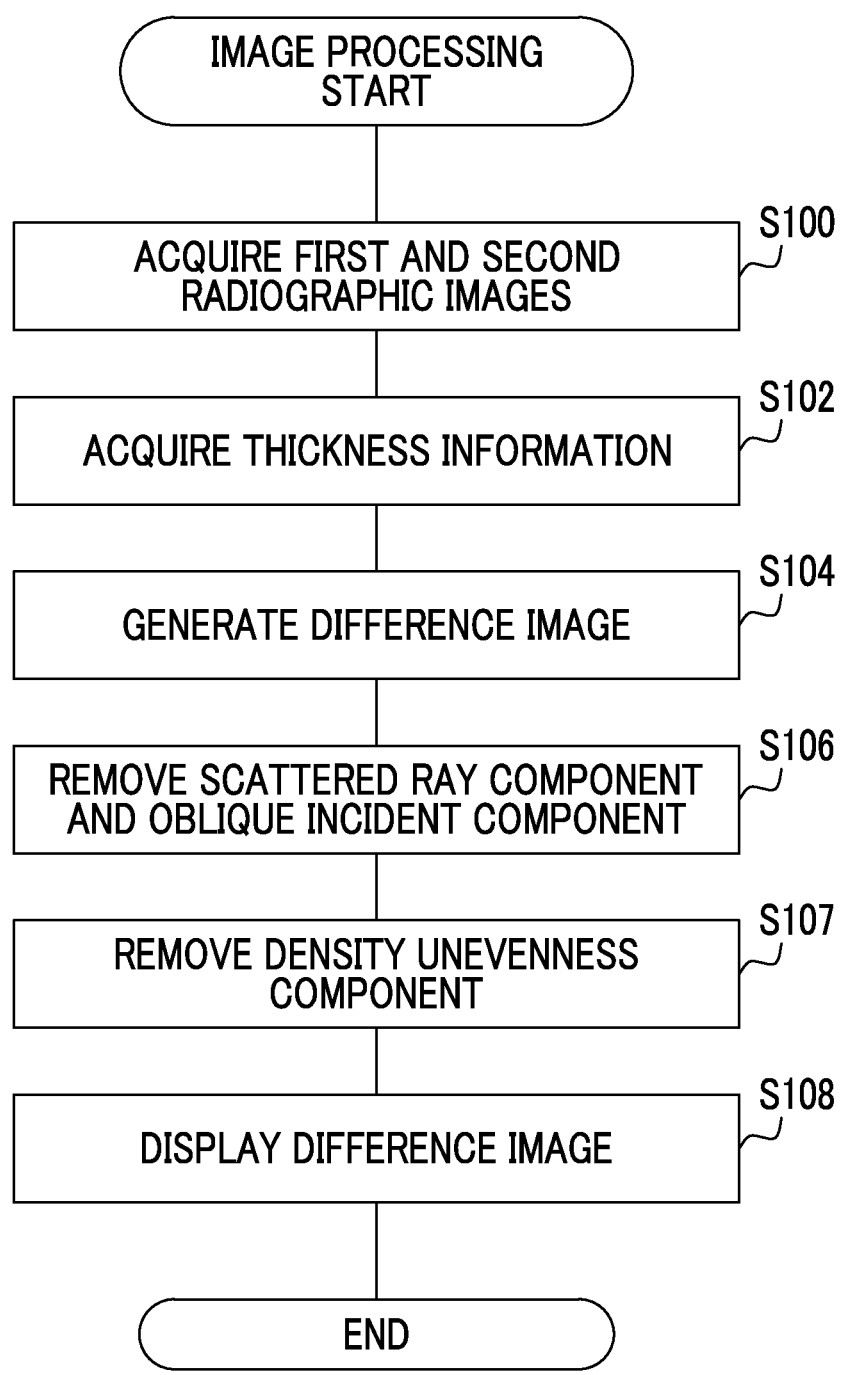
FIG. 10A is a flowchart showing another example of a flow of image processing executed on a console of the first exemplary embodiment.

FIG. 10A shows an example of the flow of image processing executed on the console 6 in this case. The image processing shown in FIG. 10A is different from the image processing of the first exemplary embodiment (refer to FIG. 7) in that the processing of Step S107 is performed between Step S106 and Step S108. In Step S107 shown in FIG. 10A, the correction unit 94 removes the density unevenness component due to the heel effect from the difference image from which the scattered ray component and the oblique incident component have been removed by the processing in Step S106. It should be noted that the order of the processing for removing the scattering component and the oblique incident component from the difference image and the processing for removing the density unevenness component due to the heel effect is not limited to the order shown in FIG. 10A, and the processing for removing the density unevenness component due to the heel effect may be performed first. In this case, similar processing may be provided between Step S104 and Step S106 instead of the processing in Step S107. In this way, the correction unit 94 may be in the aspect of removing the density unevenness component due to the heel effect from the difference image.

In addition, another example of the flow of image processing executed on the console 6 in this case is shown in FIG. 10B. The image processing shown in FIG. 10B is different from the image processing of the third exemplary embodiment (refer to FIG. 9) in that the processing of Step S103C is performed between Step S103B and Step S104. In Step S103C shown in FIG. 10B, the correction unit 94 removes the density unevenness component due to the heel effect from each of the first radiographic image and the second radiographic image from which the scattered ray component and the oblique incident component have been removed by the processing of Step S103A and Step S103B. In this way, the correction unit 94 may be in the aspect of removing the density unevenness component due to the heel effect from each of the first radiographic image and the second radiographic image.

In addition, the correction unit 94 may remove at least one component of the above-described artifact components from either the first and second radiographic images or the difference image.

In the present exemplary embodiment, the breast W is described as an example of the subject, but the subject is not limited to the breast W. For example, the subject may be a human abdomen, a thigh, or the like, and is not limited to a human being, and may be another animal.

In each of the above exemplary embodiments, for example, the following various processors can be used as a hardware structure of the processing unit that executes various processing such as the acquisition unit 90, the generation unit 92, and the correction unit 94. The various processors include, for example, a programmable logic device (PLD), such as a field-programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (program) to function as various processing units as described above.

One processing unit may be configured by one of the various processors or a combination of the same or different types of two or more processors (for example, a combination of a plurality of FPGAs or a combination of a CPU and an FPGA). In addition, the plurality of processing units may be configured by one processor.

As an example in which a plurality of processing units are configured by one processor, first, there is an aspect in which one processor is configured by a combination of one or more CPUs and software as typified by a computer, such as a client or a server, and this processor functions as a plurality of processing units. The second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above exemplary embodiments, the aspect in which the image processing program 71 is stored (installed) in the storage unit 72 has been described, but the present invention is not limited thereto. The image processing program 71 may be provided in a form recorded on a recording medium, such as a compact disc read only memory (CD-ROM), a digital versatile disc read only memory (DVD-ROM), or a universal serial bus (USB) memory, and then provided. In addition, the image processing program 71 may be downloaded from an external apparatus via the network.

For example, the configurations and operations of the radiographic imaging system 1, the console 6, and the mammography apparatus 10 described in each of the above exemplary embodiments are examples and may be changed according to the situation, without departing from the scope and spirit of the invention. In addition, each of the above exemplary embodiments may be appropriately combined with each other.

The disclosure of JP2018-173715 filed Sep. 18, 2018 is incorporated herein by reference in its entirety.

All of the documents, patent applications, and technical standards described herein are incorporated herein by reference to the same extent as a case in which the individual documents, patent applications, and technical standards were specifically and individually indicated to be incorporated by reference.

What is claimed is:

1. An image processing apparatus comprising,
a memory, and
a processor coupled to the memory, the processor configured to:
  acquire a first radiographic image captured by irradiating a subject, in a state in which a contrast agent is administered, with radiation of a first energy and a second radiographic image captured by irradiating the subject with radiation of a second energy different from the first energy and with a same imaging angle as the first radiographic image;
  perform a correction on each of the acquired first and second radiographic images to correct an oblique incident component caused by an oblique incidence of the radiation onto the subject with a correction amount corresponding to a length of a transmission path of the radiation within the subject, and to remove a scattered ray component caused by a scattered ray of radiation; and
  generate a difference image between the first radiographic image and the second radiographic image,
wherein the processor is further configured to apply a filter that removes a frequency component based on a thickness of the subject with respect to an incidence direction of the radiation.

2. The image processing apparatus according to claim 1, wherein the processor is configured to perform further correction to remove density unevenness caused by a radiation irradiation apparatus that irradiates the subject with the radiation.

3. The image processing apparatus according to claim 1, wherein the subject is a human breast.

4. An image processing method executed by a computer, the method comprising:
  acquiring a first radiographic image captured by irradiating a subject, in a state in which a contrast agent is administered, with radiation of a first energy and a second radiographic image captured by irradiating the subject with radiation of a second energy different from the first energy and with a same imaging angle as the first radiographic image;
  performing a correction on each of the acquired first and second radiographic images to correct an oblique incident component caused by an oblique incidence of the radiation onto the subject with a correction amount corresponding to a length of a transmission path of the radiation within the subject, and to remove a scattered ray component caused by a scattered ray of radiation; and
  generating a difference image between the first radiographic image and the second radiographic image,
wherein the method further comprises applying a filter that removes a frequency component based on a thickness of the subject with respect to an incidence direction of the radiation.

5. A non-transitory computer readable medium storing an image processing program for causing a computer to execute a process, the process comprising:
  acquiring a first radiographic image captured by irradiating a subject, in a state in which a contrast agent is administered, with radiation of a first energy and a second radiographic image captured by irradiating the subject with radiation of a second energy different from the first energy and with a same imaging angle as the first radiographic image;
  performing a correction on each of the acquired first and second radiographic images to correct an oblique incident component caused by an oblique incidence of the radiation onto the subject with a correction amount corresponding to a length of a transmission path of the radiation within the subject, and to remove a scattered ray component caused by a scattered ray of radiation; and
  generating a difference image between the first radiographic image and the second radiographic image,
wherein the process further comprises applying a filter that removes a frequency component based on a thickness of the subject with respect to an incidence direction of the radiation.

* * * * *